United States Patent [19]

Waterhouse et al.

[11] Patent Number: 6,014,213
[45] Date of Patent: Jan. 11, 2000

[54] HIGH DYNAMIC RANGE APPARATUS FOR SEPARATION AND DETECTION OF POLYNUCLEOTIDE FRAGMENTS

[75] Inventors: Paul Waterhouse, Copetown; Alexandre M. Izmailov, Toronto; Henryk Zaleski, Niagara Falls; John A. Renfrew, Burlington; James W. Cassidy, Waterloo, all of Canada

[73] Assignee: Visible Genetics Inc., Toronto, Canada

[21] Appl. No.: 08/819,910

[22] Filed: Mar. 18, 1997

Related U.S. Application Data

[63] Continuation-in-part of application No. PCT/US95/15951, Dec. 12, 1995, and application No. 08/452,719, May 30, 1995, which is a continuation-in-part of application No. 08/353,932, Dec. 12, 1994.

[51] Int. Cl.⁷ .................................................. G01N 21/00
[52] U.S. Cl. ........................ 356/344; 204/461; 204/466; 204/612
[58] Field of Search ...................... 356/344, 244; 204/229 R, 461, 466, 612; 436/172

[56] References Cited

U.S. PATENT DOCUMENTS

| | | | |
|---|---|---|---|
| 3,916,197 | 10/1975 | Fulwyler | 356/335 |
| 4,329,591 | 5/1982 | Fujiwara et al. | 250/548 |
| 4,343,991 | 8/1982 | Fujiwara et al. | 250/227 |
| 4,811,218 | 3/1989 | Hunkapiller | 364/413.01 |
| 4,823,007 | 4/1989 | Hanson | 250/327.2 |
| 4,832,815 | 5/1989 | Kambara et al. | 204/299 R |
| 4,881,812 | 11/1989 | Ohkubo et al. | 356/344 |
| 4,927,265 | 5/1990 | Brownlee | 356/73 |
| 4,930,893 | 6/1990 | Manian | 356/344 |
| 4,960,999 | 10/1990 | McKean et al. | 250/461.1 |
| 4,981,977 | 1/1991 | Southwick et al. | 548/455 |
| 5,006,210 | 4/1991 | Yeung et al. | 204/180.1 |
| 5,045,172 | 9/1991 | Guzman | 204/299 R |
| 5,051,162 | 9/1991 | Kambara et al. | 204/299 R |
| 5,062,942 | 11/1991 | Kambara et al. | 204/299 R |
| 5,069,769 | 12/1991 | Fujimiya et al. | 204/182.8 |

(List continued on next page.)

FOREIGN PATENT DOCUMENTS

| | | |
|---|---|---|
| 454286 | 10/1991 | European Pat. Off. . |
| 0483460 | 6/1992 | European Pat. Off. . |
| 0592060 | 4/1994 | European Pat. Off. . |
| 2411361 | 9/1975 | Germany . |
| 8707719 | 11/1987 | WIPO . |
| 94/03631 | 2/1994 | WIPO . |

OTHER PUBLICATIONS

Smith et al., "Sequence Detection in Automated DNA Analysis," *Nature* 321: 674–679 (1986).

(List continued on next page.)

*Primary Examiner*—Frank G. Font
*Assistant Examiner*—Roy M. Punnoose
*Attorney, Agent, or Firm*—Oppedahl & Larson LLP

[57] ABSTRACT

A high dynamic range apparatus for separation and detection of polynucleotide fragments has a housing adapted to receive an electrophoresis gel holder containing an electrophoresis gel loaded with fluorophore-labeled samples; one or more laser diodes for providing radiation of a frequency suitable for excitation of the fluorophore which irradiates a an array of excitation/detection sites on the electrophoresis gel; an array of detectors aligned with the excitation/detection sites for collecting fluorescent emissions; and one or more components for increasing the dynamic range of the instrument by at least an order of magnitude. These components, which can be used individually or in combination include detectors that are connected to a signal processing system that modulates the period of signal integration employed so that large signals are totaled at short time intervals and smaller signals are totaled at longer time intervals; the use of a beam splitter to produces a high intensity beam of emitted light and a low intensity beam of emitted light from each excitation/detection site; and a device for modulating the intensity of the excitation beam can be used to improve the dynamic range of the instrument.

23 Claims, 8 Drawing Sheets

U.S. PATENT DOCUMENTS

| | | | |
|---|---|---|---|
| 5,091,652 | 2/1992 | Mathies et al. | 250/458.1 |
| 5,100,529 | 3/1992 | Fuji | 204/299 R |
| 5,108,179 | 4/1992 | Myers | 356/344 |
| 5,119,316 | 6/1992 | Dam et al. | 364/498 |
| 5,122,345 | 6/1992 | Tabor et al. | 422/116 |
| 5,162,654 | 11/1992 | Kostichka et al. | 250/458.1 |
| 5,171,534 | 12/1992 | Smith et al. | 422/82.05 |
| 5,190,632 | 3/1993 | Fujiyama et al. | 204/299 R |
| 5,207,880 | 5/1993 | Middendorf | 204/182.2 |
| 5,208,466 | 5/1993 | Pentoney, Jr. | 250/574 |
| 5,213,673 | 5/1993 | Fujiyama et al. | 204/299 R |
| 5,230,781 | 7/1993 | Middendorf et al. | 204/182.2 |
| 5,242,567 | 9/1993 | Fujiyama et al. | 204/299 R |
| 5,246,866 | 9/1993 | Nasu et al. | 436/94 |
| 5,268,486 | 12/1993 | Waggoner et al. | 548/427 |
| 5,274,240 | 12/1993 | Mathies | 250/458.1 |
| 5,290,419 | 3/1994 | Kambara et al. | 204/229 R |
| 5,294,323 | 3/1994 | Togusari et al. | 204/299 R |
| 5,307,148 | 4/1994 | Kambara et al. | 356/344 |
| 5,314,602 | 5/1994 | Kambara et al. | 204/299 R |
| 5,324,401 | 6/1994 | Yeung et al. | 204/180.1 |
| 5,360,523 | 11/1994 | Middendorf et al. | 204/182.2 |
| 5,365,455 | 11/1994 | Tibbetts et al. | 364/497 |
| 5,410,412 | 4/1995 | Gombocz et al. | 356/417 |
| 5,419,825 | 5/1995 | Fujii | 204/299 |
| 5,420,691 | 5/1995 | Kawaguchi | 356/375 |
| 5,439,578 | 8/1995 | Dovichi et al. | 356/344 |
| 5,534,125 | 7/1996 | Middendorf et al. | 204/612 |
| 5,736,410 | 4/1998 | Zarling et al. | 436/172 |

OTHER PUBLICATIONS

Hjerten, S., "Free zone electrophoresis" in *Chromatographic Reviews* 9: 122–219 (1967).

Li et al., "On–the–Fly Frequency–Domain Fluorescence Lifetime Detection in Capillary Electrophoresis" *Anal. Chem.* 68: 2737–2743 (1996).

Luckey et al., "High Speed DNA Sequencing in Capillary Electrophoresis" *Nucl. Acids. Res.* 18: 4417–4421 (1990).

HIGH DYNAMIC RANGE APPARATUS FOR SEPARATION AND DETECTION OF POLYNUCLEOTIDE FRAGMENTS

STATEMENT OF RELATED APPLICATIONS

This application is related to concurrently filed U.S. patent application Ser. No. 08/819,912 which related-application is incorporated herein by reference.

This application is a continuation-in-part of PCT/US95/15951 filed Dec. 12, 1995 and U.S. patent application Ser. No. 08/452,719 filed May 30, 1995, which is a CIP of 08/353,932 filed Dec. 12, 1994, which applications are incorporated herein by reference.

BACKGROUND OF THE INVENTION

This invention relates to a high dynamic range apparatus for separation and detection of polynucleotide fragments which is particularly useful in performing the method for quantifying and partially sequencing a nucleic acid analyte that is present in a sample as disclosed in related U.S. patent application Ser. No. 08/819,912. In this method, a nucleic acid-containing sample is combined with a control polynucleotide and then amplified with multiple primer sets to produce control nucleic acid fragment generated by amplification of the control polynucleotide, conserved nucleic acid fragments generated by amplification of a conserved region of the nucleic acid in the sample to produce a quantitative measure of the presence of a target nucleic acid in the sample, and sequencing fragments preferably generated by amplification of a more variable portion of the nucleic acid in the sample which, upon sequencing, can provide information concerning and/or discrimination among different but closely related forms of a target nucleic acid, including but not limited to different allelic or mutant forms of genes, or in the case of microorganisms, subspecies, serovars, strains, sub-types, biovars, variants, or serotypes or between closely related species of the target. The resulting fragments are separated by size, for example by polyacrylamide gel electrophoresis (PAGE) and the control and conserved fragments are detected by fluorescence from a label attached to the amplification primer.

Depending on the differential amounts of control and target nucleic acid present in the sample, the magnitudes of the signals corresponding to the control and conserved fragments may differ by several orders of magnitude. In the past, because instruments used for measuring fluorescence from electrophoresis gels have had a relatively low dynamic range, this has generally meant that the replicate experiments at different dilutions must be performed to permit both a peaks to be measured. Such dilutions increase the cost of an assay, because of increased time required to prepare the sample and decreased instrumental throughput, and can be a source of error in the quantitation of the amount of material in the sample since serial dilutions necessitate both precise preparation and a post-measurement calculation to arrive at a quantitative result.

To maximize the ability to obtain quantitative results for the amount of a target nucleic acid in a sample, without having to perform serial dilutions, it would be desirable to have an apparatus for electrophoretic separation and real-time detection of nucleic acids which had a high dynamic range, for example on the order of $10^4$ to $10^6$ or more. It is an object of the present invention to provide such an apparatus.

SUMMARY OF THE INVENTION

The present invention provides a high dynamic range apparatus for nucleic acid sequencing comprising:

(a) a housing adapted to receive an electrophoresis gel holder containing an electrophoresis gel loaded with fluorophore-labeled samples;

(b) one or more laser diodes for providing radiation of a frequency suitable for excitation of the fluorophore;

(c) means for directing the radiation to a plurality of excitation/detection sites on the electrophoresis gel;

(d) an array of detectors aligned with the excitation/detection sites for collecting fluorescent emissions and producing an electrical output signal indicative of the intensity of the fluorescent emissions; and (e) means for increasing the dynamic range of the apparatus by at least one order of magnitude. In a first embodiment of the invention, the detectors are connected to a signal processing system that modulates the period of signal integration employed so that large signals are totaled at short time intervals and smaller signals are totaled at longer time intervals, thus increasing the dynamic range. In a second embodiment of the invention, a beam splitter which produces a high intensity beam of emitted light and a low intensity beam of emitted light from each excitation/detection site and directs one beam to each of two detectors associated with the excitation/detection site. In a third embodiment of the invention, modulation of the intensity of the excitation beam can be used to improve the dynamic range of the instrument. An excitation beam of alternating high and low intensity can be used, and measurements are made during either the low power windows or the high power windows, depending on the strength of the signal. Depending on the recovery time of the detector employed and the dwell time of a migrating electrophoresis band within the excitation/detection site, this embodiment can use either a single or multiple detectors per site. A duty cycling of alternating on and off periods of varying times can also be used, particularly in cases where the minimum integration period of the detector may be too long for detection of very large peaks.

BRIEF DESCRIPTION OF THE DRAWINGS

FIGS. 2A and 1B show alternative means for directing the excitation radiation to an array of excitation/detection sites;

DETAILED DESCRIPTION OF THE INVENTION

The present invention relates to a high dynamic range apparatus for nucleic acid sequencing comprising:

(a) a housing adapted to receive an electrophoresis gel holder containing an electrophoresis gel loaded with fluorophore-labeled samples;

(b) one or more laser diodes for providing radiation of a frequency suitable for excitation of the fluorophore;

(c) means for directing the radiation to a plurality of excitation/detection sites on the electrophoresis gel;

(d) an array of detectors aligned with the excitation/detection sites for collecting fluorescent emissions and producing an electrical output signal indicative of the intensity of the fluorescent emissions; and (e) means for increasing the dynamic range of the apparatus by at least one order of magnitude. The apparatus can be used for separation and detection of polynucleotide fragments, such as fragments generated in a nucleic acid amplification or sequencing reaction, a restriction fragment length polymorphism (RFLP) assay or a single-stranded conformational polymorphism (SSCP) assay, as well as any other test in which the separation and detection of polynucleotide fragments is required. The apparatus of the invention is particularly suitable for use in separating and detecting polynucleotides fragments in mixtures where several different polynucleotide fragments may be present in widely differing amounts. Thus, for example, the apparatus of the invention is well-suited for separating and detecting the polynucleotide fragments produced in the method disclosed in related U.S. patent application Ser. No. 08/819,912.

Figure 1A:
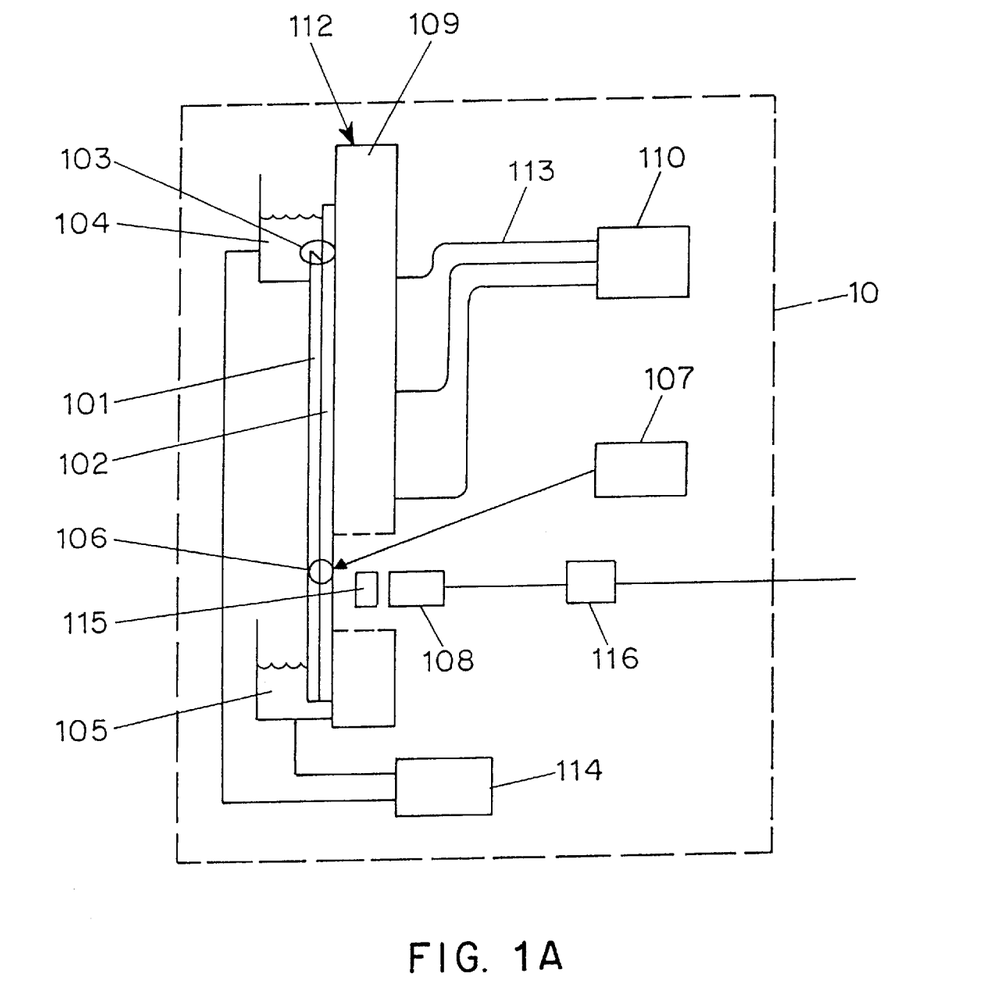
FIGS. 1A and 1B show apparatus in accordance with the invention.

FIG. 1A illustrates the basic structure of an apparatus of the invention. As shown, the apparatus has a housing 10 within which the means for electrophoretic separation and detection of the sample are disposed. The housing 10 advantageously provides a sealed, light tight environment in which the processing of the sample is conducted.

Within the housing 10, a loaded electrophoresis gel 102 within a gel holder 101 is positioned on a mounting plate 109 which holds the gel in a fixed position relative to the remainder of the apparatus, including the excitation/detection portions of the apparatus. The loaded gel may be held in place using suction through the mounting plate 109 generated using suction pump 110 and tubing 113, although other methods of holding the loaded gel in place may be used.

Opposing ends of the loaded gel 102 are placed in contact with two electrodes, such as solution electrodes 104 and 105. These electrodes are connected to a power supply 114 which generates an electric field within the gel. This field causes the sample to migrate in the gel from loading site 103 towards excitation/detection site 106.

An excitation source 107 which supplies electromagnetic radiation having a frequency effective to excite the fluorophore used as a label is disposed within the housing 10 such that radiation from the excitation source 107 is directed to strike the gel at the excitation/detection sites 106. A multiple beam splitter 202 may be employed to generate a plurality of spots in a linear array, one spot at each excitation/detection site on a planar electrophoresis gel. Alternatively, a linear array of excitation/detection sites can be generated by an array of laser diodes, each diode disposed to deliver excitation energy to a single excitation/detection site. In either case, fluorescence emissions from fluorophore-labeled molecules at the excitation/detection site are collected using optical system 115 and detected using detector 108. The analog output signal from detector 108 may then be converted to a digital signal using an A-to-D converter 116, and output for further processing and/or display.

Figure 1B:
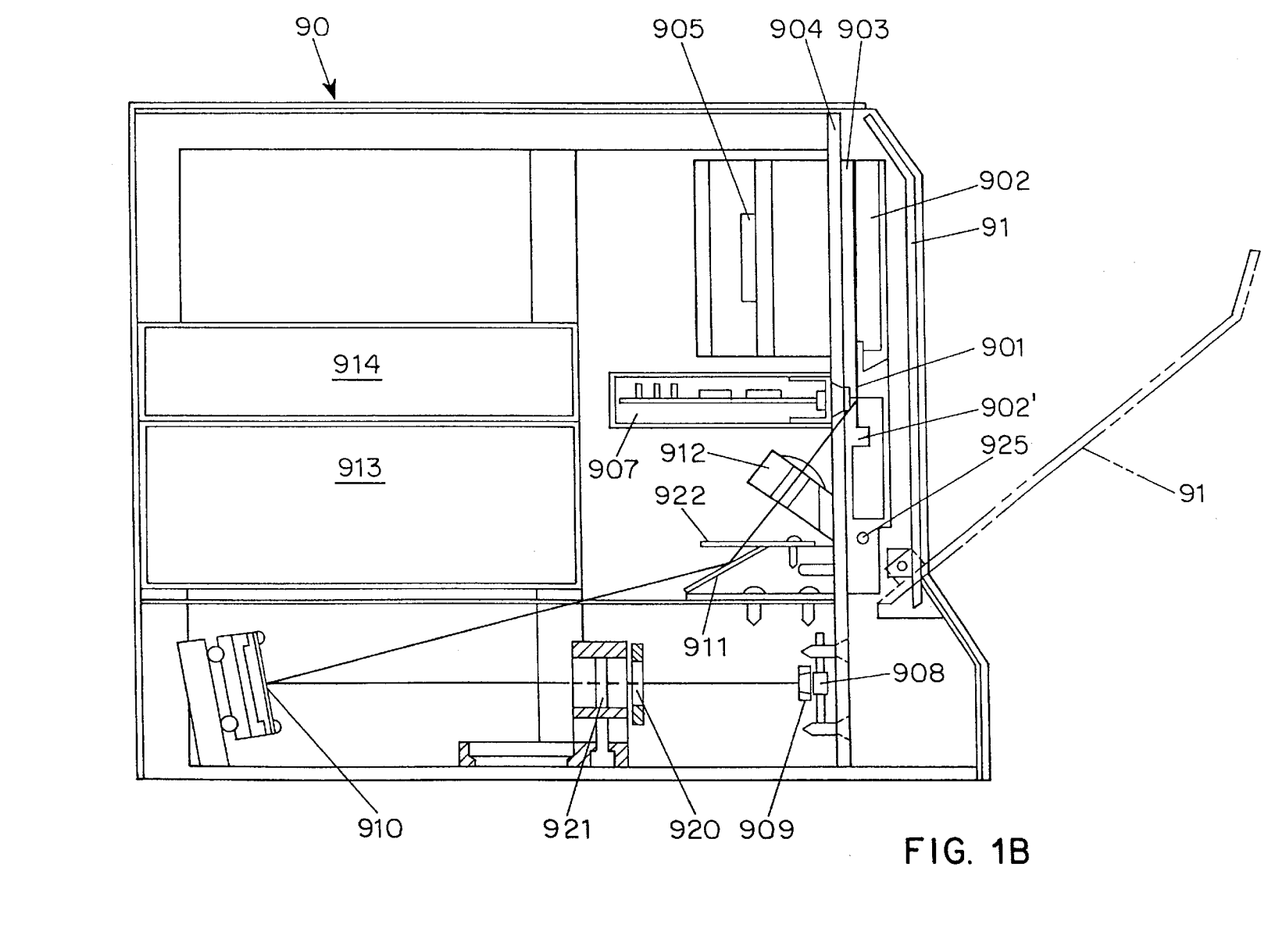

FIG. 1B shows a cross-section of a further embodiment of the apparatus of the invention. The various components of the apparatus are disposed within a housing 90, which has a access door 91 the front thereof. The access door 91 is hinged to permit movement between a closed position (solid line) and an open position (dashed line).

Within the housing 90, the gel holder 901 is held in position between two solution electrodes 902, 902' against mounting plate 903. The mounting plate 903 and the solution electrodes pivot outward on pin 925 to facilitate loading of an electrophoresis gel. A heating element 904 is disposed in thermal contact with the back surface of the mounting plate 903 to permit heating of the gel. A fan 905 which is surrounded to a sub-housing 906 and vented to the exterior of the housing 90 blows room temperature air across the back of the heating element 904. Through a combination of heating and cooling provided by the heating element 904 and fan 905, respectively, a desired temperature in the range of from 30 to 55 degrees C. can be maintained to a tolerance of 0.5 degrees.

A detector module 907 consisting of an array of photodiodes, each connected to a circuit board is aligned with the excitation detection site in the gel, and collects light which is emitted perpendicular to the surface of the gel holder 901. The circuit board contains an analog-to-digital (A/D) converter which converts the analog current output of the diode to a digital voltage signal. This digital signal may then be further processed by the computer circuit board 914 disposed within the housing or transmitted to an external computer for processing.

The excitation beam is provided by a laser diode 908 mounted in alignment with an aspherical lens 909. The aspherical lens 909 collimates the output from the laser diode 908 and directs it towards a beam splitter, in this case a transmissive diffraction grating 920, which divides the light from the laser diode into 16 beamlets of substantially equal intensity. These beamlets are conducted by lens 921 and mirrors 910, 911 to a cylindrical lens 912 which forms the squashed spots at the excitation/detection sites. The mirrors 910, 911 may be aluminum or aluminum coated glass when the excitation wavelength is below 650 nm, but are advantageously gold coated glass for longer wavelengths because of the greater reflectivity of gold at these wavelengths. Dielectric mirrors may also be used although they are substantially more expensive.

Within the apparatus shown in FIG. 1B, there is also an apertured barrier 922 between the last mirror 911 and the cylindrical lens 912 aligned so that each beamlet passes through an individual hole (1–3 mm diameter) in the barrier. This barrier reduces the amount of scattered light which reaches the excitation detection site.

A power supply 913 is disposed within the housing 90 and is connected to the solution electrodes 902 to provide the voltage gradient for electrophoresis.

Figure 2A:
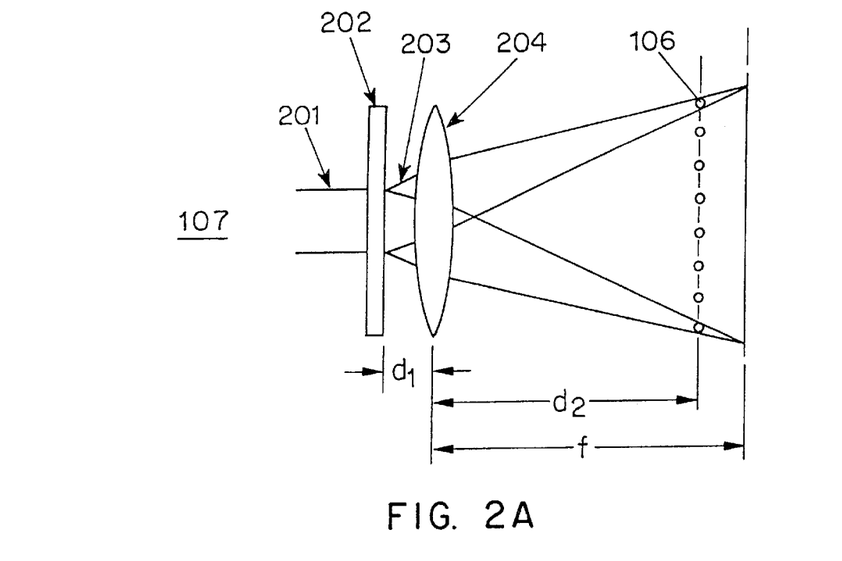

FIG. 2A shows the operation of the beam splitter 202 (920 in FIG. 1B) in more detail. Radiation 201 from an excitation source 107 is directed to the excitation site 106 by use of a multiple beam splitter 202, such as a Spot Array Generation Grating, which splits the incident beam into a number of beamlets, generally from 2 to 24 beamlets. Preferred diffraction gratings are of the type known as "transmissive" or "phase" gratings, because such gratings can be designed to produce an even intensity distribution of light among the resulting beamlets. In the illustrated embodiment, an incident laser beam of a frequency suitable for excitation of the fluorophore is directed into a binary phase grating, approximately 1 cm square, mounted on glass, thermoplastic or the like of approximately 1/8th inch thickness (Semiconductor Technology Inc, Pointe Claire, Quebec). The transmitted beam is divided into a linear array of the desired number of excitation beamlets, 203, one for each intended excitation/detection site, 106. The beamlets are directed to a focusing lens, 204 (e.g., Stock # G69, 129, Catalog 1994, Edmund Scientific). The focusing lens has in the embodiment shown preferably has a focal distance, f, of 505 mm. The spot at each excitation site can be varied in size by changing the distance, $d_2$ between the lens and the excitation site. The spots are suitably between 0.1 mm and 0.2 mm diameter. In a preferred embodiment, the spot array generation grating divides the incident laser beam into a linear array of 16 spots, and the lens is disposed between 200 to 500 mm from the gel.

As an alternative to the embodiment shown in FIG. 2A, the focusing lens 204 can be omitted. In this case, beam 201 is slightly convergent as it illuminates the diffraction grating 202 so that the incident radiation is focused on the gel surface.

A preferred spot array generation grating for use in an apparatus with 16 lanes is a 1 to 16 beam-splitter such as that available from Dinova Optics, Quebec, Canada (Part No. QP 960101-6). Spot array generation gratings which split an incident beam into a greater or lesser number of spots with the same wavelength characteristics as the incident beam may be employed to provide irradiation to apparatus with larger or smaller numbers of lanes. Several spot array generation gratings can also be used in parallel with several associated light sources, for example two 1 to 16 beam-splitters and two laser diodes can be used for a 32 lane apparatus.

Figure 2B:
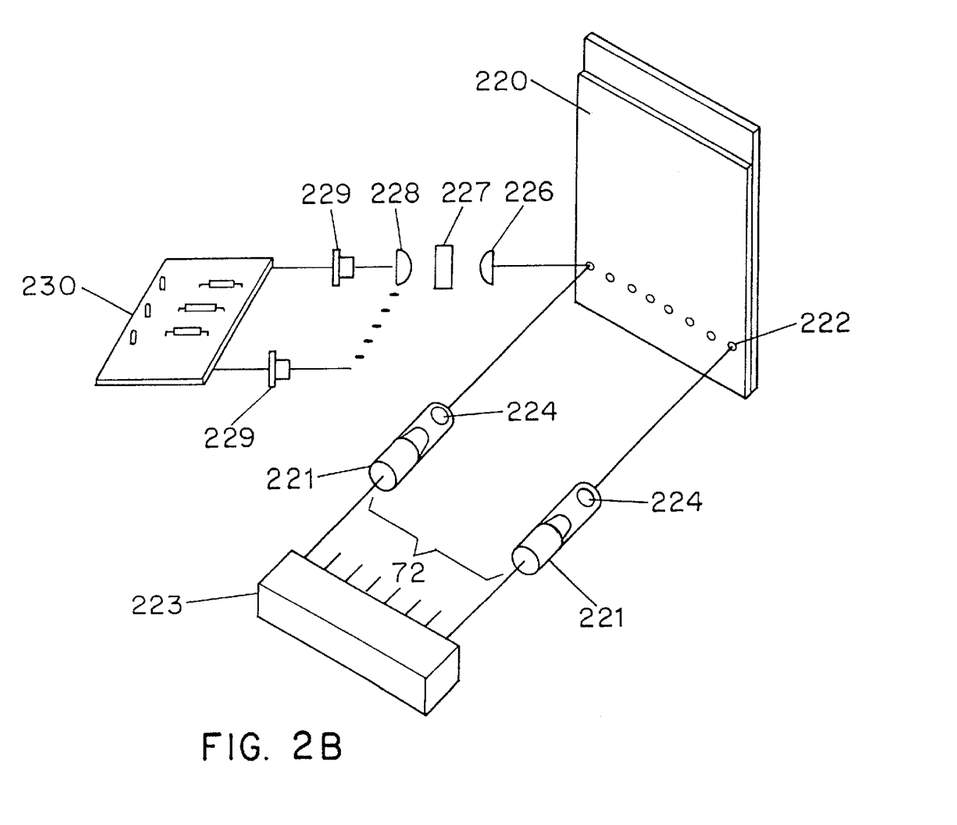

An alternative method for generating a linear array of spots on a planar gel 220 is illustrated in FIG. 2B. In this method, a dedicated laser diode 221 is disposed to deliver electromagnetic radiation to each excitation/detection site 222. The laser diodes 221 are assembled in an array. Each laser diode 221 may have its own power supply 223 with independent adjustment of current, or the power supplied may be linked.

Light from each laser diode 221 is passed through a spheric lens 224 to direct it to the corresponding excitation/detection site 222 on the gel 220. Emitted light from each excitation/detection site 222 is collected by a lens 226, filtered by an optical filter 227 to remove stray light of the excitation wavelength and then directed by lens 228 to a photodiode detector 229. The detectors 229 are connected to an electrical circuit board 230 for processing of the detector output.

In the apparatus of the invention, the source of excitation radiation is a laser diode having a wavelength suitable for excitation of a fluorophore affixed to the polynucleotide fragments being analyzed. In the case of the fluorescent label Cy5.5, a suitable source of excitation radiation is a Phillips 20 mW laser diode (part No. CQL806/D) producing light with a wavelength of 675–677 nm. Emitted light is passed through a 695–735 nm bandpass filter (Omega Optical, Brattleboro, Vt.), and detected using an array of Silicon photodiode detectors (Hamamatsu Photonics, Hamamatsu City, Japan, Part No. S2386-18K)

The means for increasing the dynamic range incorporated in the apparatus of the invention is effective to increase the dynamic range of the instrument by at least an order of magnitude relative to the same instrument lacking this element. Various means for increasing the dynamic range may be employed.

In a first embodiment of the invention, the detectors are connected to a signal processing system that has two distinct periods of signal integration, i.e., two distinct periods during which the detector is permitted to accumulate signal before it is sampled or read. When the intensity of the emitted light is high, the detector may be saturated in a relatively short period of time. A short integration period permits the detection of meaningful signal before this saturation occurs. On the other hand, when the emitted light intensity is low, a longer integration period may be required. By alternating short and long integration periods the detector can therefore provide a broader dynamic range. The preferred range of short to long periods is between 1:1000 and 1:10, and preferably 1:100. A suitable minimum period is 10 mS, and a suitable long period would be 1 sec. The sampling periods are separated by the time needed to sum the detector, approximately 1 mS. This technique is disclosed more fully in U.S. patent application Ser. No. 08/452,719. In general, however, the integration period is determined by a microprocessor which determines when to sample the photodiode detector. Specifically the photodiode generates a current proportional to the photons detected. The current accumulates in a capacitor which is part of an integrator. The voltage on the capacitor is sampled (or read) by an A/D converter at the times determined by the microprocessor, can then discharged and reset after sampling. Alternatively, after reading the value at the end of the short integration period, the integrator can continue accumulating counts without discharging and resetting the capacitor until the end of the long integration period, at which time the integrator is sampled (or read) and then discharged and reset. In this embodiment, the short integration period overlaps in time with the long integration period. In either case, the integrator transmits the sampled value as a data point for further processing.

Figure 3A:
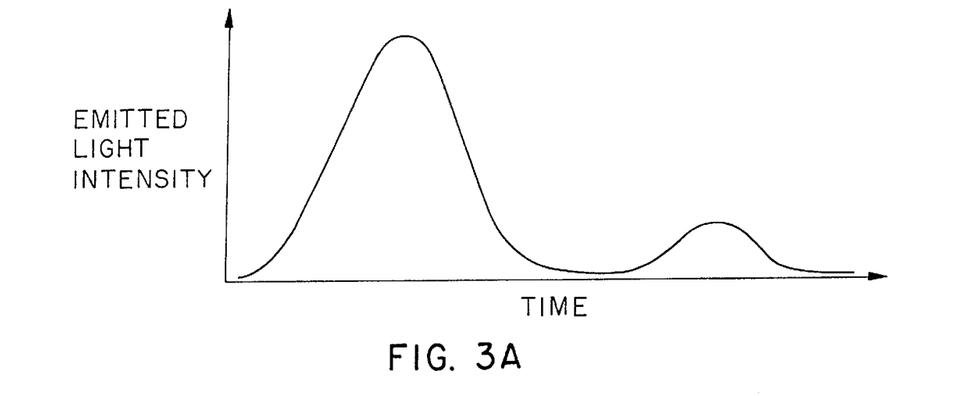
FIGS. 3A–3C illustrate the peak size, collected light intensity and detector signal for an embodiment of the invention.
Figure 3B:
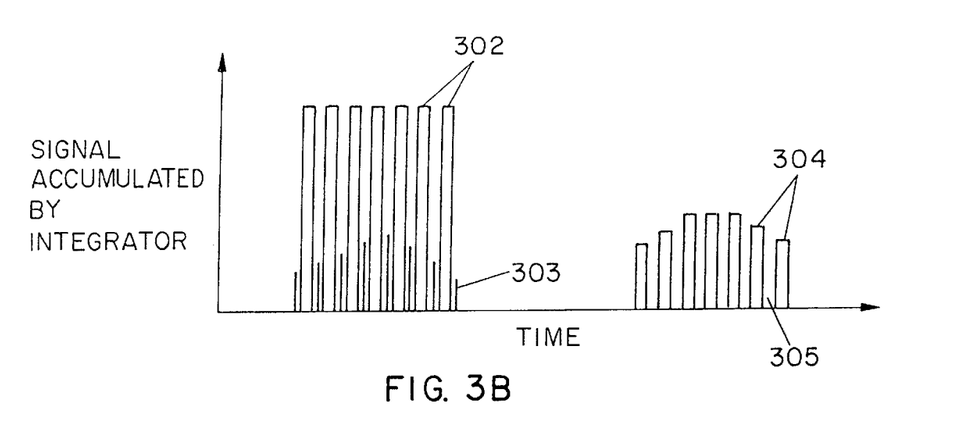
Figure 3C:
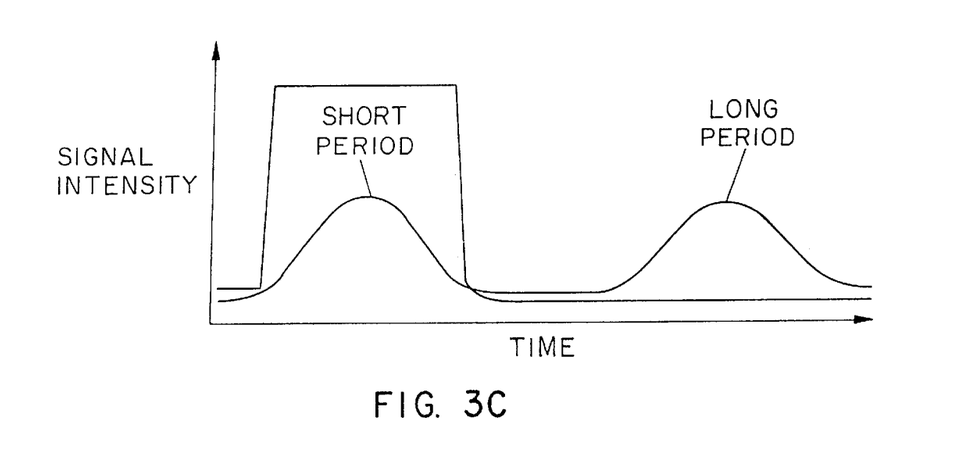

FIG. 3A shows a plot of emitted light intensity as a function of time for a sample containing a peak 300 of high intensity and a peak 301 of low intensity. FIG. 3B shows the signal (counts) accumulated by the detector as a function of time, when the detector is sampled with alternating long periods (for example 988 mS) and short periods (for example 10 mS) with a gap (of for example 1 mS) for sampling and resetting after each period. When the large sample peak 300 is passing through the detection site, the detector becomes saturated when the long integration time is used, resulting in a truncated peak 302. On the other hand, the short integration periods result in workable numbers of counts being accumulated as reflected by peak 303. Conversely, when the small peak is in the detection site, the long integration period produces workable levels of counts as reflected by peaks 304, while the short integration peak essentially fails to accumulate any counts above the background as reflected by the troughs 305. The accumulated signals from the detector produce two data traces as shown in FIG. 3C. Taken together, after correction for the differences in accumulation period, these two traces provide information about all of the peaks in the sample.

This technique can be used to provide a substantial increase in dynamic range which depends on the difference between the long integration period and the short integration period. In general, two integration periods are sufficient to increase the dynamic range of an apparatus according to the invention to cover the entire range which might be needed to evaluate separated DNA fragments. In the event very high dynamic range is required, it may be desirable to use three or more integration periods of varying length to produce three or more data traces which are corrected for the difference in integration period and then combined.

Figure 4:
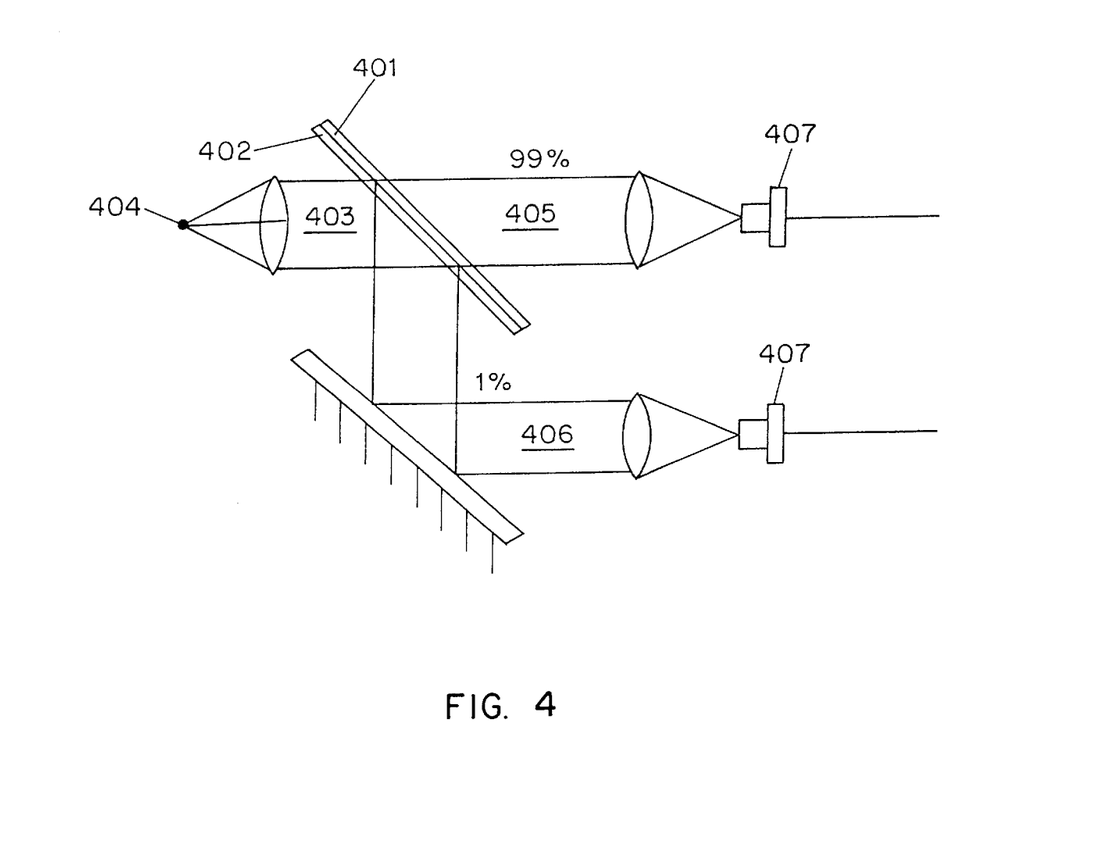
FIG. 4 shows a second embodiment of the means for increasing the dynamic range of the apparatus of the invention.

FIG. 4 shows a second embodiment of the invention in which a beam-splitter 401, such as a glass plate, with or without an anti-reflection coating 402, divides emissions 403 from the excitation/detection site 404 into majority 405 and minority 406 fractions. As shown, each fraction can be quantified with its own detector 407. Alternatively, a chopper can be used to transmit light from the two beams alternately to a single detector. By linking the frequency with which the accumulated photon count is collected from the detector with the frequency with which the chopper transmits two signals corresponding to the two portions of the divided emission beam can be generated.

This embodiment of the invention is capable of providing enhancements in the dynamic range of an instrument of about 1 to 2 orders of magnitude depending on the differential between the beams produced by the beam splitter. A flat glass plate will reflect about 4% of the beam on each surface and allow 92% transmission; with an anti-reflective coating this differential can be increased to 1% to 99%. Highly reflective mirror which deflects 95% of the light and allows 5% transmission can also be used. In either case the minority beam detector generally gives useful results in the linear range for detection when the majority beam saturates its detector, and the majority beam can generally provide detection even when the minority beam is too weak.

Figure 5A:
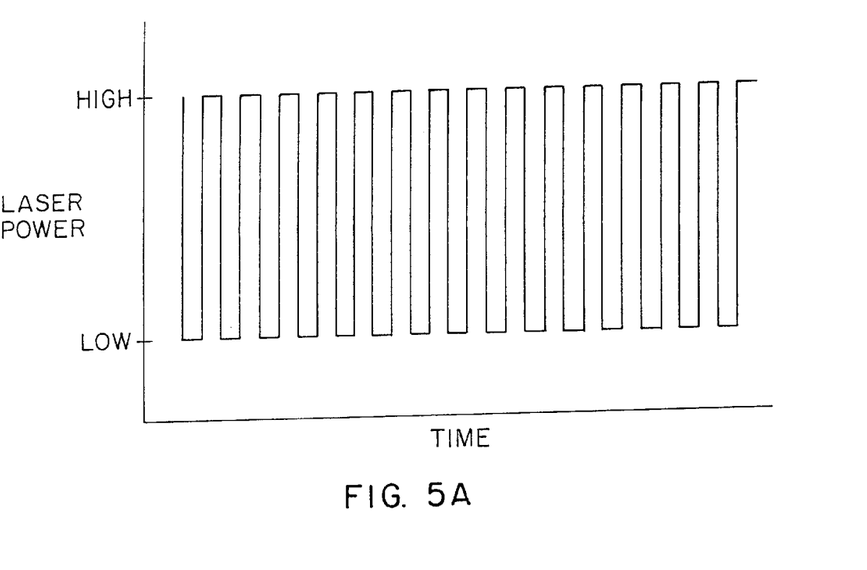
FIGS. 5A–5D illustrate the use of a modulated excitation beam in accordance with the present invention.
Figure 5B:
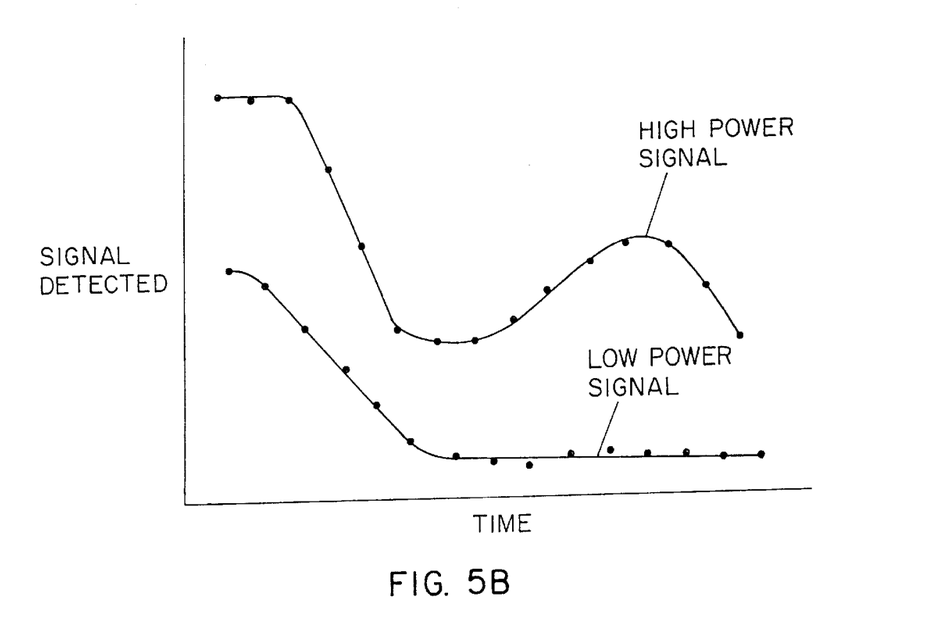

FIGS. 5A and B illustrate a third embodiment of the invention in which modulation of the intensity of the excitation beam is used to improve the dynamic range of the instrument. The power of semiconductor lasers can be modulated very precisely. A For example, a Phillips 20 mW laser diode can be rapidly modulated across the range of 1–20 mW by employing a standard electrical pulse generator, having the required depth of modulation, to create the levels of electric current through the laser diode which produce the desired high and low intensity levels. The output intensity is linearly related to electric current over an output range of 0.5 to 20 mW for these laser diodes.

By modulating the output of the laser diode in a square-wave function as shown in FIG. 5A between a high intensity excitation beam (for example 20 mW) and a low intensity excitation beam (for example 1 mW) and separately detecting the emitted light produced in response to the high and low intensity portions of the excitation beam, provided that the sample in the excitation site behaves in the linear range (i.e. no quenching or bleaching), a 20 fold improvement in the dynamic range of the apparatus can be obtained. Other oscillating functions, for example a sine wave, can also be used in place of the square wave function.

Separate detection of the emitted light produced in response to the high and low intensity portions of the excitation beam to produce two data traces as shown in FIG. 5B can be accomplished using two detectors for each excitation/detection site, or it can be accomplished using a single detector with the accumulated signal being collected from the detector in synchronous fashion with the frequency of the square-wave modulation of the excitation beam.

The apparatus of the invention can incorporate any one of the several means for increasing the dynamic range of apparatus, or it can incorporate more than one of these several means in combination. By combining all three means in a single apparatus, a dynamic range improvement on the order of four to five orders of magnitude or more can be obtained.

Figure 5C:
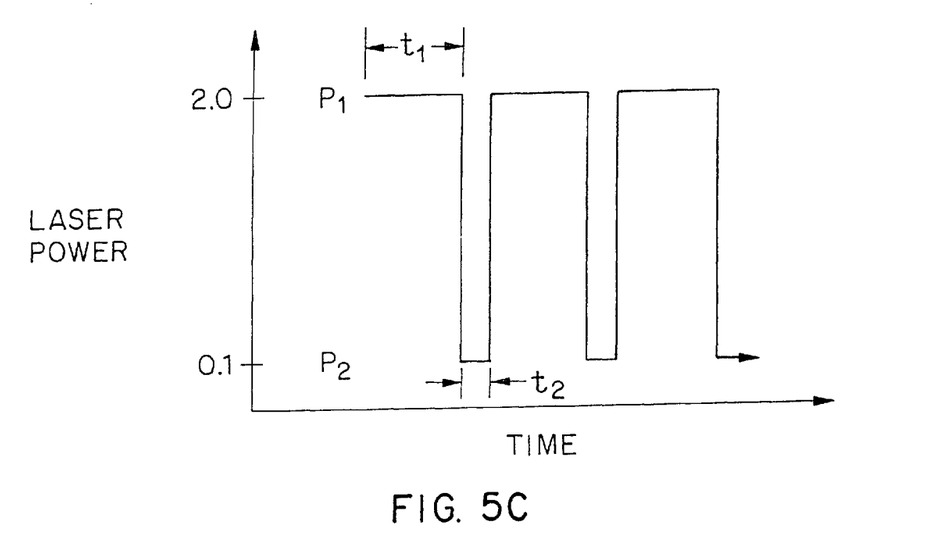

For example, in a preferred embodiment of the apparatus according to the invention modulation of the excitation beam is combined with the use of long and short integration periods to increase the dynamic range of the apparatus. Preferably, the periods of high and low intensity are coordinated with the periods of long and short integration periods, respectively. Thus, as illustrated in FIG. 5C, the laser power is set to a high level $P_1$ (most suitable for observation of small peaks) for a period of time $t_1$ in synchronicity with a long integration period (also most suitable for observation of small peaks). The laser power is then reduced to a low level $P_2$ for a short period of time $t_2$ in synchronicity with a short integration period to provide a regime suitable for the observation of large peaks. The dynamic range in such an apparatus is increased by an amount equal to $P_1 t_1 / P_2 t_2$.

Figure 5D:
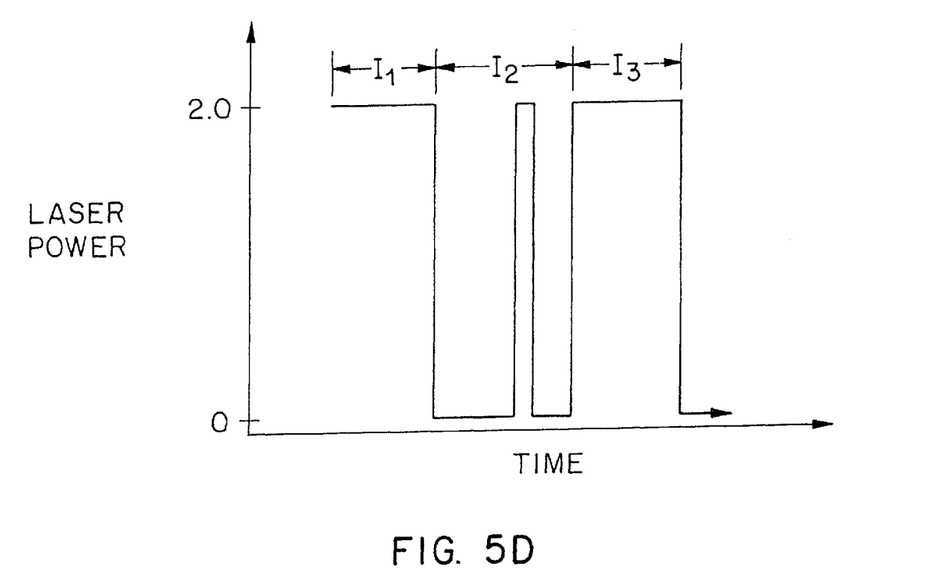

Modulation of the input radiation between an on state and an off state can also be used to increase the dynamic range of the instrument. This approach can be used with instruments having a single integration period as shown in FIG. 5D, where the laser power is on during all of integration periods $I_1$ and $I_3$, but only during a fraction of integration period $I_2$. This approach can also be used in combination with variable integration periods, and is particularly useful where the shortest integration period which can be achieved by a detector/integrator combination is still to long to permit quantitative measurement of a very intense peak. By shortening the duration of exposure to excitation energy during the short integration period the number of counts accumulated during this period is further reduced, thus increasing the ability of the apparatus to quantitate large peaks.

Figure 6A:
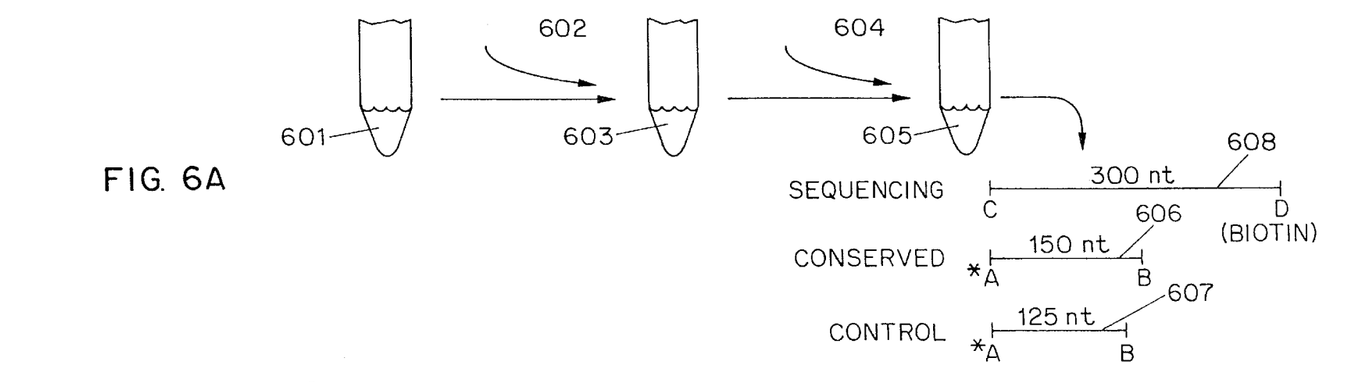
FIGS. 6A and 6B illustrate a method in which the apparatus of the invention is suitably employed.
Figure 6B:
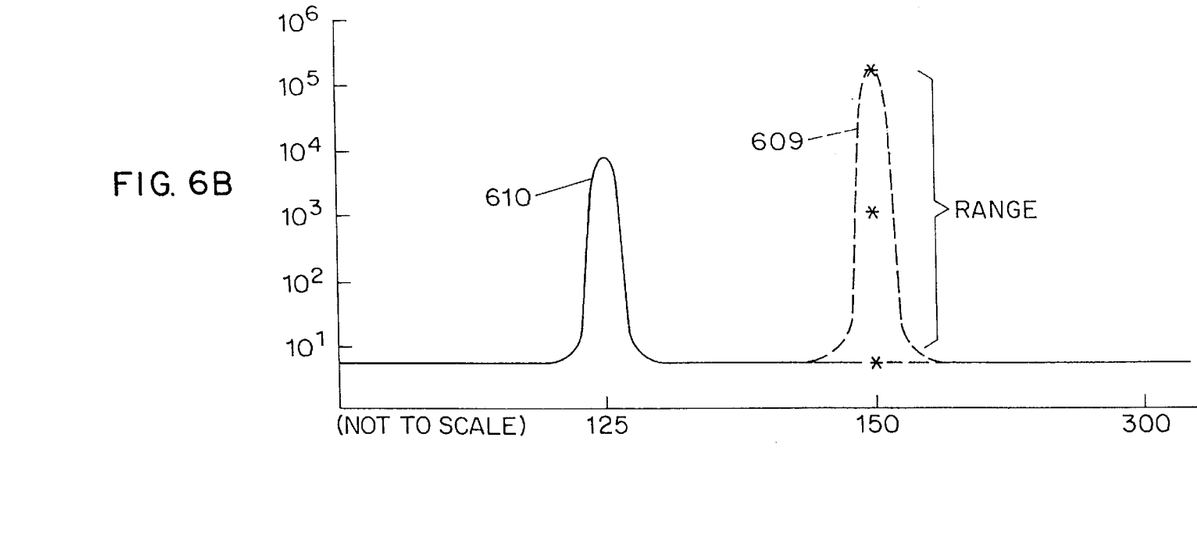

The apparatus of the present invention is particulary well-suited to performing separation and detection of polynucleotide fragments where fragments of different sizes may be present in significantly different amount. This can occur, for example, in assays where a control nucleic acid is added to a sample and then coamplified. Such a method is illustrated in FIGS. 6A–6B. Total nucleic acids (DNA or RNA) 601 are prepared from a known amount of patient sample. The preparation 601 is mixed with a control nucleic acid 602 of known quantity to create a reaction pre-mixture 603. The pre-mixture 603 is treated with reagents 604 to create an amplification reaction mixture 605 if the sample is DNA, or if the preparation is RNA, reagents 604 are combined to create a combined reverse transcription and amplification reaction mixture 605. In either case, two pairs of amplification primers A, B and C, D are added to the amplification mixture 605.

The first primer pair (A, B) specifically hybridizes with the sense and antisense strands of a conserved region of the nucleic acid analyte and the control nucleic acid 602. One primer of the first pair (A, B) is conjugated at its 5'-end to a detectable label, such as a fluorescent label. The second primer pair (C, D) specifically hybridizes with the sense and antisense strands of a second distinct region of the nucleic acid analyte that is separate and distinct from the conserved region and suitable for typing by sequence analysis. One primer of the second pair (C, D) is conjugated at its 5'-end to biotin, or a similar label which permits physical capture of the primer.

When the amplification reagents 604 are added, and the resulting reaction mixture 605 is thermally cycled for amplification, three amplified reaction products are generated if the nucleic acid analyte is present in the patient sample. The two amplified reaction products expected from the first primer pair are i) a fragment 606 of fixed length from a region of the analyte that is highly conserved among all varieties or sub-types of the pathogen (the "conserved fragment"); and ii) a fragment 607 of a different length that is generated from the control nucleic acid (the "control fragment"). These two fragments are detectably labeled. The amplification product of the second primer pair extends across a region of high variability or clinical relevance among varieties or subtypes of the pathogen (the "sequencing fragment"). This fragment 608 is generally longer than the other two, and it is labeled with biotin or similar label which permits the physical capture of the sequencing fragment.

Quantitation is performed by loading part of the reaction mixture on an apparatus in accordance with the present invention and applying an electric field to separate amplified fragments according to their size. The peaks 609, 610 corresponding to conserved and control fragments 606, 607 are quantified by measuring the area under each peak of the output signal (FIG. 6B). Because the control fragment is added in known amount, the amount of nucleic acid in the original patient sample can be calculated by extrapolation. The sequencing fragment is not detected at this step, but is instead used as the starting point for a subsequent sequencing step for qualitative evaluation of the nature of the nucleic acid in the sample.

Each apparatus configuration within the scope of the present invention may exhibit a different relationship between the amount of polynucleotide present and the fluorescence intensity measured over the broad dynamic range which may be of interest. For example, a 100-fold increase in sample may lead to a 100-fold increase in signal for an apparatus in one configuration and only a 10-fold increase in signal in another configuration. Thus, each apparatus configuration is initially calibrated to determine this relationship for the apparatus by evaluating serial dilutions of a standard sample of known concentration. This calibration may be incorporated in a data processing system provided with the apparatus, or may be performed by the user.

We claim:

1. An electrophoresis separation and real-time detection apparatus comprising:
   (a) a housing adapted to receive an electrophoresis gel holder containing an electrophoresis gel loaded with fluorophore-labeled samples;
   (b) one or more laser diodes for providing radiation of a frequency suitable for excitation of the fluorophore;
   (c) means for directing the radiation to a plurality of excitation/detection sites on the electrophoresis gel;
   (d) an array of detectors aligned with the excitation/detection sites for collecting fluorescent emissions and producing an electrical output signal indicative of the intensity of the fluorescent emissions; and
   (e) means for increasing the dynamic range of the apparatus by at least one order of magnitude.

2. The apparatus according to claim 1, wherein the means for increasing the dynamic range comprises an integrator for producing an integrated output signal from the detector, said integrator integrating over alternating long intervals and short intervals, the long intervals being at least ten times longer than the short intervals.

3. The apparatus according to claim 2, wherein the long intervals are at least 100 times longer than the short intervals.

4. The apparatus according to claim 1, wherein the means for increasing the dynamic range comprises a beam splitter which produces a high intensity beam of emitted light and a low intensity beam of emitted from each excitation/detection site.

5. The apparatus according to claim 4, wherein the high intensity beam is at least ten times as intense as low intensity beam.

6. The apparatus according to claim 4, wherein two detectors in the array of detectors are aligned with each excitation/detection site, a first of said detectors being aligned to detect the high intensity beam and a second of said detectors being aligned to detect the low intensity beam.

7. The apparatus according to claim 4, wherein the means for increasing the dynamic range further comprises an integrator responsive to the output signal and producing an integrated output signal therefrom, said integrator integrating over alternating long intervals and short intervals, the long intervals being at least ten times longer than the short intervals.

8. The apparatus according to claim 7, wherein the long intervals are at least 100 times longer than the short intervals.

9. The apparatus according to claim 1, wherein the means for increasing the dynamic range comprises means for modulating the intensity of the excitation source between a high intensity level and a low intensity level.

10. The apparatus according to claim 9, wherein the intensity of the excitation source is modulated in a square wave function.

11. The apparatus according to claim 9, wherein the means for increasing the dynamic range further comprises an integrator responsive to the output signal and producing an integrated output signal therefrom, said integrator integrating over alternating long intervals and short intervals, the long intervals being at least ten times longer than the short intervals.

12. The apparatus according to claim 11, wherein the long intervals are at least 100 times longer than the short intervals.

13. The apparatus according to claim 11, wherein the means for increasing the dynamic range further comprises a beam splitter which produces a high intensity beam of emitted light and a low intensity beam of emitted from each excitation/detection site.

14. The apparatus according to claim 13, wherein the high intensity beam is at least ten times as intense as low intensity beam.

15. The apparatus according to claim 13, wherein two detectors in the array of detectors are aligned with each excitation/detection site, a first of said detectors being aligned to detect the high intensity beam and a second of said detectors being aligned to detect the low intensity beam.

16. The apparatus according to claim 13, wherein the means for increasing the dynamic range further comprises an integrator responsive to the output signal and producing an integrated output signal therefrom, said integrator integrating over alternating long intervals and short intervals, the long intervals being at least ten times longer than the short intervals.

17. The apparatus according to claim 16, wherein the long intervals are at least 100 times longer than the short intervals.

18. The apparatus according to claim 9, wherein the means for increasing the dynamic range comprises a beam splitter which produces a high intensity beam of emitted light and a low intensity beam of emitted from each excitation/detection site.

19. The apparatus according to claim 18, wherein the high intensity beam is at least ten times as intense as low intensity beam.

20. The apparatus according to claim 18, wherein two detectors in the array of detectors are aligned with each excitation/detection site, a first of said detectors being aligned to detect the high intensity beam and a second of said detectors being aligned to detect the low intensity beam.

21. The apparatus according to claim 2, wherein the means for increasing the dynamic range comprises a beam splitter which produces a high intensity beam of emitted light and a low intensity beam of emitted from each excitation/detection site.

22. The apparatus according to claim 21, wherein the high intensity beam is at least ten times as intense as low intensity beam.

23. The apparatus according to claim 21, wherein two detectors in the array of detectors are aligned with each excitation/detection site, a first of said detectors being aligned to detect the high intensity beam and a second of said detectors being aligned to detect the low intensity beam.

* * * * *